US012778979B2

(12) United States Patent
Fälker et al.

(10) Patent No.: US 12,778,979 B2
(45) Date of Patent: Nov. 3, 2026

(54) TREATMENT OF PATIENTS UNDER ANTIPLATELET MEDICATION EXPERIENCING ACUTE BLEEDING COMPLICATIONS DURING/AFTER SURGERY

(71) Applicant: Knut Fälker, Vintrosa (SE)

(72) Inventors: Knut Fälker, Vintrosa (SE); Karl Magnus Lennart Grenegård, Linköping (SE); Nils Peter Påhlsson, Linköping (SE); Mats Olof Dreifaldt, Kumla (SE)

(73) Assignee: Knut Fälker, Vintrosa (SE)

( * ) Notice: Subject to any disclaimer, the term of this patent is extended or adjusted under 35 U.S.C. 154(b) by 1211 days.

(21) Appl. No.: 17/625,618

(22) PCT Filed: Jul. 9, 2020

(86) PCT No.: PCT/EP2020/069417

§ 371 (c)(1),
(2) Date: Jan. 7, 2022

(87) PCT Pub. No.: WO2021/005169

PCT Pub. Date: Jan. 14, 2021

(65) Prior Publication Data

US 2022/0257639 A1 Aug. 18, 2022

(30) Foreign Application Priority Data

Jul. 11, 2019 (SE) .................................... 1950885-2

(51) Int. Cl.
*A61K 31/737* (2006.01)
*A61K 36/03* (2006.01)
*A61P 7/04* (2006.01)

(52) U.S. Cl.
CPC ............ *A61K 31/737* (2013.01); *A61K 36/03* (2013.01); *A61P 7/04* (2018.01)

(58) Field of Classification Search
CPC ................ A61K 31/737; A61K 31/216; A61K 31/4365; A61K 31/60; A61K 36/03; A61K 45/06; A61K 45/00; A61K 9/7023; A61K 2300/00; A61P 7/02; A61P 7/04; A61F 2013/00463
USPC ........................................................... 514/59
See application file for complete search history.

(56) References Cited

U.S. PATENT DOCUMENTS

2005/0282771 A1 12/2005 Johnson

FOREIGN PATENT DOCUMENTS

| | | | | |
|---|---|---|---|---|
| JP | 2013231025 A * | 11/2013 | ........... A61K 31/737 |
| WO | 2008103234 A1 | 8/2008 | |
| WO | WO 2008/134430 A1 * | 11/2008 | ............. A61K 45/06 |
| WO | 2010066869 A2 | 6/2010 | |

OTHER PUBLICATIONS

Durig et al, Thrombosis Research, 1997, 85(6), 479-491.*
Oliveira et al, Macromolecular Bioscience, 2017, 17, 1-13.*
Tengdelius et al, Macromolecular Biosciences, 2017, 17, 1-9.*
Godier, Anne et al, Journal of Clinical Medicine, 2020, 9, 2318, pp. 1-11.*
C. Kardeby, K. Falker, E.J. Haining, M. Criel, M. Lindkvist, R. Barroso, P. Pahlsson, L.U. Ljungberg, M: Tengdelius, G.E. Rainger, S. Watson, J.A. Eble, M.F. Hoylaerts, J. Emsley, P. Konradsson, S.P. Watson, Y. Sun, M. Grenegard, Synthetic glycopolymers and natural fucoidans cause human platelet aggregation via PEAR1 and GPIbalpha, Blood Adv 3(3) (2019) 275-287, 10.1182/bloodadvances.2018024950.
M. Tengdelius, C.J. Lee, M. Grenegard, M. Griffith, P. Pahlsson, P. Konradsson, Synthesis and biological evaluation of fucoidan-mimetic glycopolymers through cyanoxyl-mediated free-radical polymerization, Biomacromolecules 15(7) (2014) 2359-68, 10.1021/bm5002312.
M. Tengdelius, C. Kardeby, K. Falker, M. Griffith, P. Pahlsson, P. Konradsson, M. Grenegard, Fucoidan-Mimetic Glycopolymers as Tools for Studying Molecular and Cellular Responses in Human Blood Platelets, Macromol Biosci 17(2) (2017), 10.1002/mabi.201600257.
Christophe Vandenbriele, Yi Sun, Maarten Criel, Katrien Cludts, Soetkin Van Kerckhoven, Benedetta Lzzi, Thomas Vanassche, Peter Verhamme, & Marc F. Hoylaerts, Dextran sulfate triggers platelet aggregation via direct activation of PEAR1, Platelets, 2015; 27(4): 365-372e 2015 Taylor & Francis. DOI: 10.3109/09537104.2015.1111321.
Caroline Kardeby, Studies of platelet signalling and endothelial cell responses using unique synthetic drugs, Örebro University, 2019.
Caroline Kardeby, Knut Fälker, Elizabeth J Haining, Maarten Criel, Madelene Lindkvist, Ruben Barroso, Peter Påhlsson, Liza U Ljungberg, Mattias Tengdelius, G Ed Rainger, Stephanie Watson, Johannes A Eble, Marc F Hoylaerts, Jonas Emsley, Peter Konradsson, Steve P Watson, Yi Sun, Magnus Grenegård, Synthetic glycopolymers and natural fucoidans cause human platelet aggregation via PEAR1 and GPIba, Blood Adv. Feb. 12, 2019;3(3):275-287.
Alexandre Kauskot, Michela Di Michele, Serena Loyen, Kathleen Freson, Peter Verhamme, Marc F. Hoylaerts, A novel mechanism of sustained platelet aIIbβ3 activation via PEAR1, vol. 119, Issue 17 Apr. 26, 2012.
Pan M, Suárez De Lezo J, Velasco F, Romero M, Medina A, Segura J, Hernández E, Pavlovic D, Melian F, Gallardo A, Zayas R, Ruiz M, Torres A, Reduction of thrombotic and hemorrhagic complications after stent implantation. Am Heart J. Dec. 1996; 132(6):1119-26. doi: 10.1016/s0002-8703(96)90454-8. PMID: 8969562.

(Continued)

*Primary Examiner* — Ganapathy Krishnan
(74) *Attorney, Agent, or Firm* — Renner, Otto, Boisselle & Sklar, LLP

(57) ABSTRACT

The invention pertains platelet endothelial aggregation receptor 1 (PEAR1) agonist for use in the treatment of bleeding in a patient wherein the patient is under antiplatelet medication. Provided is also a topical haemostat, a sealant, or an adhesive, to be used locally during surgery.

15 Claims, 5 Drawing Sheets

(56) References Cited

OTHER PUBLICATIONS

Hua He,Ke Bing-Bing Ke, Yan Li, Fu-Sheng Han, Xiaodong Li, Yu-Jie Zeng, Perioperative management of antithrombotic therapy in patients receiving cardiovascular implantable electronic devices:a network meta-analysis, J Interv Card Electrophysiol (2017) 50:65-83, D0110J007/s10840-017-0280-4.
Aakash Garg, Sunil V. Rao., Amit Rout, Mohammad Thawabi, Naiam Wasly Marc Cohen, Newark Beth Israel Medical Center, Effect of Potent P2Y12 Inhibitors on Safety and Efficacy of Bivaurudin Compared to Heparin in Acute Coronary Syndrome: A Meta-Analysis of Randomized Controlled Trials, 1397 JACC Mar. 20, 2018, vol. 71. Issue 11.
Bhanu Kanth Manne et al., Fucoidan Is a Novel Platelet Agonist for the C-type Lectin-like Receptor 2 (CLEC-2), the Journal of Biological Chemistry vol. 288, No. 11, pp. 7717-7726, Mar. 15, 2013.
International Search Report and Written Opinion for related International Application No. PCT/EP2020/069417 dated Sep. 22, 2020.

* cited by examiner

Impact of secreted ADP and autocrine actions via P2Y12 receptor signalling on the course of platelet aggregation

TREATMENT OF PATIENTS UNDER ANTIPLATELET MEDICATION EXPERIENCING ACUTE BLEEDING COMPLICATIONS DURING/AFTER SURGERY

This application is a national phase of International Application No. PCT/EP2020/069417, filed Jul. 9, 2020, which claims priority to Sweden Application No. 1950885-2, filed Jul. 11, 2019, the entire disclosures of which are hereby incorporated by reference.

FIELD OF THE INVENTION

This invention pertains in general to treatment of patients under antiplatelet medication using agents that modulate human blood platelet activation and aggregation. Especially patients experiencing bleeding complications during/after surgery. Furthermore, the present invention pertains to a platelet endothelial receptor 1 (PEAR1) agonist, such as natural fucoidans, synthesized fucoidan-mimetic glycopolymers such as sulfated α-L-fucoside-pendant glycopolymer, or dextran sulfate for such use.

BACKGROUND OF THE INVENTION

Human blood platelets, also colloquially designated thrombocytes, patrol the blood vessels as sentinels of vascular integrity. Platelets play a pivotal role in physiological haemostasis by adhering to the injured vessel wall, aggregation, propagation of coagulation, and thrombus formation; the latter which is also referred to as a "blood clot". Further, platelets are also subsequently involved in fibrinolysis (decomposition of the thrombus) and the repair of the vessel wall, thereby restoring blood flow and vascular integrity.

Under pathophysiological conditions such as atherosclerosis, the rupture of an atherosclerotic plaque can lead to inappropriate platelet aggregation and thrombus formation that can cause vascular occlusions resulting in acute myocardial infarction (AMI) or stroke, which are, according to the World Health Organization (WHO), the worldwide leading causes for death.

The formation of a thrombus, simplified spoken, involves two major components: Activated platelets and soluble blood constituents, the latter which are designated "coagulation factors" and in their entity form the "coagulation cascade". Activated platelets, besides releasing autocrine feed-back mediators (such as thromboxane A2 (TXA2) and adenosine diphosphate (ADP)) and building up a loose fibrinogen-bridged aggregate, change the composition and electric charge of their outer membrane into a so-called "procoagulant surface". To this surface coagulation factors bind and are transformed into their active forms, finally funneling into the conversion of fibrinogen into fibrin, thereby turning the loose platelet-aggregate into a stable thrombus.

In this respect, antithrombotic medication is separated into two major groups of pharmaceuticals. One group, the anticoagulants, targets the components of the coagulation cascade, such a heparins or vitamin K antagonists. The other group, the antiplatelet drugs, interferes directly with the initial activation of platelets. As such, anticoagulants allow for platelet aggregation but impede coagulation, whereas antiplatelet drugs hinder initial platelet activation and aggregation, and by that likewise coagulation. Anticoagulants are mostly prescribed to patients showing clinical indications which may lead to a future thrombotic event. Antiplatelet drugs, in contrast, are immediately and in a high dosage administered to patients experiencing an AMI or stroke. Patients surviving such events must often receive a lifetime treatment with antiplatelet drugs in order to prevent the recurrence of such life-threatening complications. Along this line, the combination of drugs which interfere with TXA2 synthesis and signalling (such as aspirin) and antagonists of the P2Y12 receptor for ADP (such as clopidogrel, cangrelor, or ticagrelor) represents today's "gold standard" for dual antiplatelet therapy (DAPT) to treat acute events as well as their recurrence. If such patients require surgery or dental work that can be planned in advance, a controlled temporary discontinuation of medication is the preferred practice today. However, when patients under antiplatelet medication are in vital need of instant/acute surgery bleeding complications are unavoidable.

On rare occasions, however, patients may be misdiagnosed as experiencing an AMI or stroke because of the shown symptoms and comparatively high incidence of such events and will therefore been instantly administered an ultra-high dose of a fast acting P2Y12 receptor antagonist, such as clopidogrel, cangrelor, or ticagrelor. When patients are subsequently diagnosed as experiencing for instance an acute aortic dissection (AD) instead of an AMI or stroke, immediate surgery is inevitable. The surgical method of choice is that the aorta is divided and a surgical interposition graft is sewn in. At sites of the joining between the aorta and the graft, as well as at the stitching, extended bleedings occur due to the lack of platelet aggregation, coagulation, and plug formation, as the direct result of the initial admission of an ultra-high dose of a P2Y12 receptor antagonist.

Today, no solutions exist to effectively stop bleedings under above mentioned circumstances. Existing products are topical haemostatics, sealants, and adhesives. Hemostats can clot blood. Sealants can create sealing barriers. Adhesives bond tissue together. Collagen, gelatin, and cellulose are haemostatic agents. TachoSil® is a development of TachoComb® and TachoComb®H. TachoComb is made with equine collagen, bovine thrombin, bovine aprotinin, and human fibrinogen. However, none of these products can effectively solve the bleeding complications during surgery caused by P2Y12 receptor-blocking or DAPT medication.

The lack of methods or products to solve the complications caused by P2Y12 receptor-antagonizing medication or DAPT during acute surgery often cause that patients may have to suffer several days with open chest wounds and receive a multitude of blood transfusions, which both bear the additional risk of severe infections until bleeding has stopped and before the surgeon can close the wound.

As such, there is a need for treatment strategies to tackle bleeding complications in patients under antiplatelet medication, especially for those who are in vital need of immediate surgery.

SUMMARY OF THE INVENTION

Accordingly, the present invention preferably seeks to mitigate, alleviate or eliminate one or more of the above-identified deficiencies in the art and disadvantages singly or in any combination and solves at least the above-mentioned problems by providing a platelet endothelial aggregation receptor 1 (PEAR1) agonist for use in the treatment of bleeding in a patient, wherein the patient is under antiplatelet medication.

Provided is also a topical haemostatic, a sealant, or an adhesive, to be locally applied during surgery, wherein the topical haemostatic, a sealant, or an adhesive comprises a platelet endothelial aggregation receptor 1 (PEAR1) agonist, for treating bleeding in a patient under antiplatelet medication.

BRIEF DESCRIPTION OF THE DRAWINGS

These and other aspects, features and advantages of which the invention is capable of will be apparent and elucidated from the following description of embodiments of the present invention, reference being made to the accompanying drawings, in which FIG. 1A is an illustration of acute aortic dissection (AD), showing the separation of the inner and middle layers of the aorta, B an illustration of the aorta which relates the extent of the ballooning to effected tissues, and C an illustration of an open descending thoracic aortic replacement, wherein the aorta is divided and a surgical Dacron interposition graft is sewn in.

DESCRIPTION OF EMBODIMENTS

The following description focuses on an embodiment of the present invention applicable to treatment strategies for patients who received antiplatelet medication. Especially to treatment of patients who suffer from bleeding complications during/after surgery.

In the course of physiological primary haemostasis, blood platelets instantly adhere to the denuded sub-endothelium at the site of vascular injury, become activated and release autocrine mediators such as thromboxane A2 (TXA2) and adenosine diphosphate (ADP), enable the conformation of the fibrinogen-receptor integrin αIIbβ3 into an activated state, and finally aggregate to build a fibrinogen-bridged plug. For TXA2 the thromboxane/prostanoid receptor-α (TPα) is the predominant isoform on platelets and, like the receptors for thrombin (PAR-1 and PAR-4), couples to Gα12/13 and Gαq. For ADP the Gαq-coupled P2Y1 receptors and Gαi2-coupled P2Y12 receptors have been identified on platelets. Signalling via the (β/γ-subunit of Gαi is known to be associated with the amplification of granule secretion as well as the activation of integrin αIIaβ3 (known as 'inside-out' signalling) whereas the α-subunit down-regulates adenylyl cyclase (AC) and therefore cyclic adenosine monophosphate (cAMP) levels, all which is pivotal for full and sustained platelet activation and aggregation.

Figure 2:
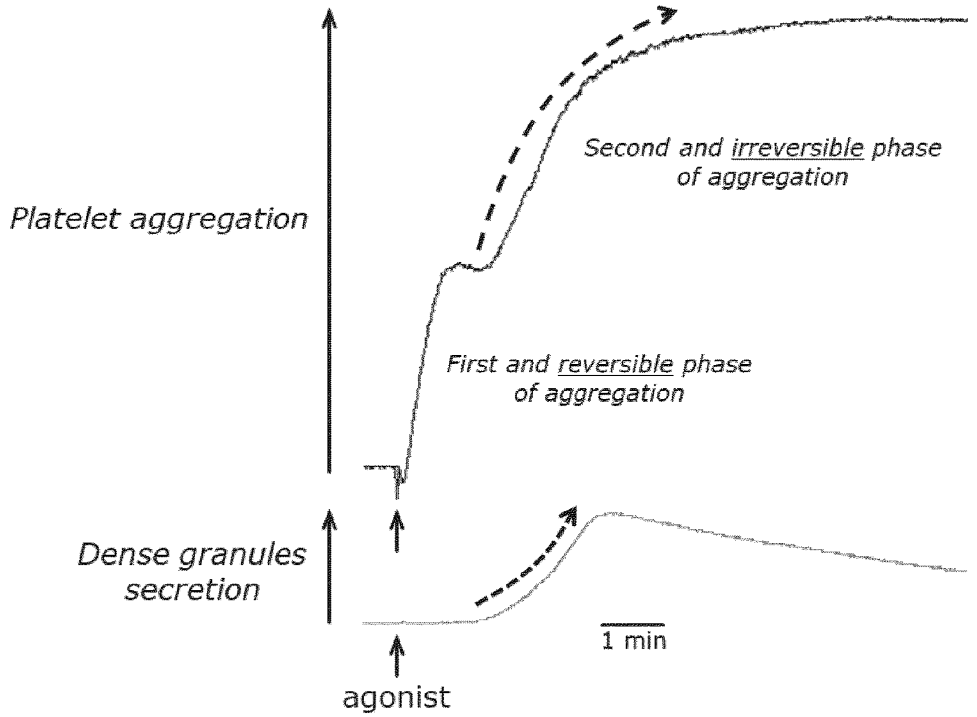
FIG. 2 shows original traces exemplifying the two phases of human platelet aggregation (upper trace) and the impact of secreted ADP from dense granules (lower trace) and autocrine actions via P2Y12 receptor signalling on the second and irreversible phase of platelet aggregation.

Human platelet aggregation induced by a physiological agonist, as exemplified in FIG. 2, is characterized by two phases. The first phase is induced by the primary agonist itself and is, in case the stimulus is too weak to provoke the release of autocrine feedback mediators like ADP from dense granules, reversible due to de-activation of the fibrinogen-receptor integrin αIIaβ3. When the primary stimulus is strong enough to induce ADP secretion, the autocrine actions of ADP via P2Y12 receptor signalling amplifies and enhances platelet responses including the activation of the integrin αIIaβ3 resulting in a second and irreversible phase of platelet aggregation.

Whereas platelet activation and aggregation induced by primary platelet agonists to various degrees depend on intermediate TXA2 generation and autocrine signalling, all known physiological platelet agonists so far, regardless their initial signaling cascades employed, crucially depend on ADP release and subsequent P2Y12 signaling. The combined inhibition of TXA2/TPα-signalling by e.g. aspirin and ADP/P2Y12-signalling by e.g. ticagrelor represents today's "gold standard" for anti-thrombotic therapy. Most, if not all, patients who experienced an AMI or stroke are under this dual anti-platelet therapeutic regime (DAPT) to prevent the recurrence of a thrombotic event.

Figure 3:
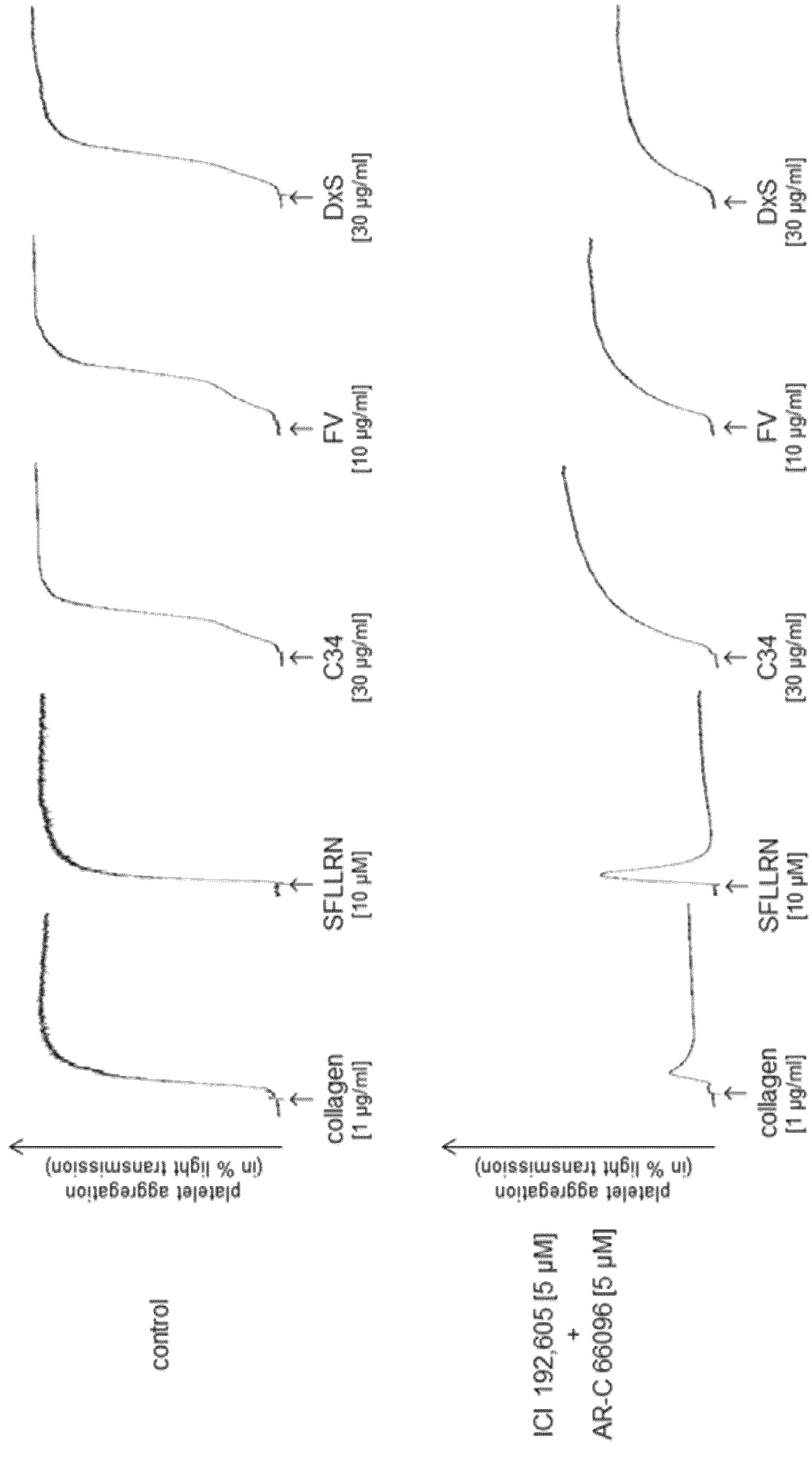
FIG. 3 shows original traces of aggregation in terms of light transmission in plasma of non-pretreated (control) platelets as well as of platelets pretretated with both the potent TPα receptor antagonist ICI 192,605 and widely in vitro applied P2Y12 receptor antagonist AR-C 66096 stimulated with collagen and the thrombin-mimetic SFLLRN, which both account for known physiological platelet agonists, as well as the synthetic sulfated α-L-fucoside-pendant glycopolymer with average monomeric units of 34 fucose molecules (C34), natural fucoidan from *F. vesiculosus* (FV), or dextran sulfate (DxS).

Thus, for patients under antiplatelet therapies, the first phase of platelet aggregation may occur, but, as illustrated in FIG. 2, this first phase is reversible. The effect of this is shown in FIG. 3, where dual platelet inhibition (blocking TPα/TXA2 and P2Y12/ADP receptors) allow for only the first but reversible phase of platelet aggregation in response to collagen and the thrombin-mimetic and PAR-1 activating hexapeptide SFLLRN.

In patients receiving antiplatelet medication platelet aggregation is prevented or reversible. When these patients require instant or acute surgery, bleeding complications to various extents are inevitable.

Fucoidans, polysulfated fucose polysaccharides of varying chain-length from natural sources have so far been suggested to be used in a clinical setting for having either pro-coagulatory or anti-coagulatory properties, depending on the observations reported or stated. However, a precise mode of action on molecular levels has been elusive. In WO 2008103234, it was suggested that purified fucodians may be used as an anti-coagulant to subjects with pro-thrombotic conditions like deep vein thrombosis, arterial thrombosis, and other cardiovascular diseases.

The effects of fucoidans on blood platelet activation and aggregation are far less developed. It has previously been reported that natural fucoidan isolated from *F. vesiculosus* induces human and murine platelet activation and aggregation via the C-type Lectin-like receptor 2 (Clec-2). In studies related to this disclosure, these findings could not be reproduced, and the platelet endothelial receptor 1 (PEAR1) was instead identified as the main receptor provoking human platelet activation and aggregation by natural fucoidan as well as synthetic sulfated α-L-fucoside-pendant glycopolymers [1]. Previous to identifying the involvement of PEAR-1, it was shown that synthetic sulfated α-L-fucoside-pendant glycopolymers are potent agonists of human platelet activation and aggregation [2, 3]. However, PEAR1 has been reported to be likewise activated by dextran sulfate; the latter which was therefor included in studies related to this disclosure as a positive control for PEAR1 induced signalling. In Kauskot et. al. [4], a PEAR1 extracellular domain protein (abbreviated PEAR1-EC) was shown to induce aggregation of washed (isolated) human platelets in a concentration-dependent fashion, however, nothing pointed to possible clinical applications of a PEAR1-EC.

Along this line, the endogenous ligand for PEAR1 in humans as well as other species still remains to be elucidated.

With respect to the two phases of platelet aggregation mentioned above and illustrated in FIG. 2, it was observed that natural fucoidan (from *F. vesiculosus*) and the synthetic sulfated α-L-fucoside-pendant glycopolymer with a chain length of 34 monomers (C34) induced the ‘classic’ bi-phasic course of platelet aggregation in plasma. Similar traces were observed when platelets with dextran sulfate were stimulated (FIG. 3).

Further, in the presence of receptor antagonists which interfere with TXA2/TPα and ADP/P2Y12 signalling (dual inhibition) primary and reversible platelet aggregation caused by collagen and the thrombin-mimetic PAR-1 activating hexapeptide SFLLRN has been observed to various extends, and, as expected, a lack of the second and irreversible phase.

In sharp contrast, and most noteworthy, as disclosed herein, it was shown that natural fucoidan (from *F. vesiculosus*), the synthetic sulfated α-L-fucoside-pendant glycopolymer with a chain length of 34 monomers (C34), as well as dextran sulfate provoke the first phase of platelet aggregation, which to our very surprise remained irreversible and sustained in the presence of both TPα and P2Y12 antagonists (dual inhibition; DAPT).

Figure 4:
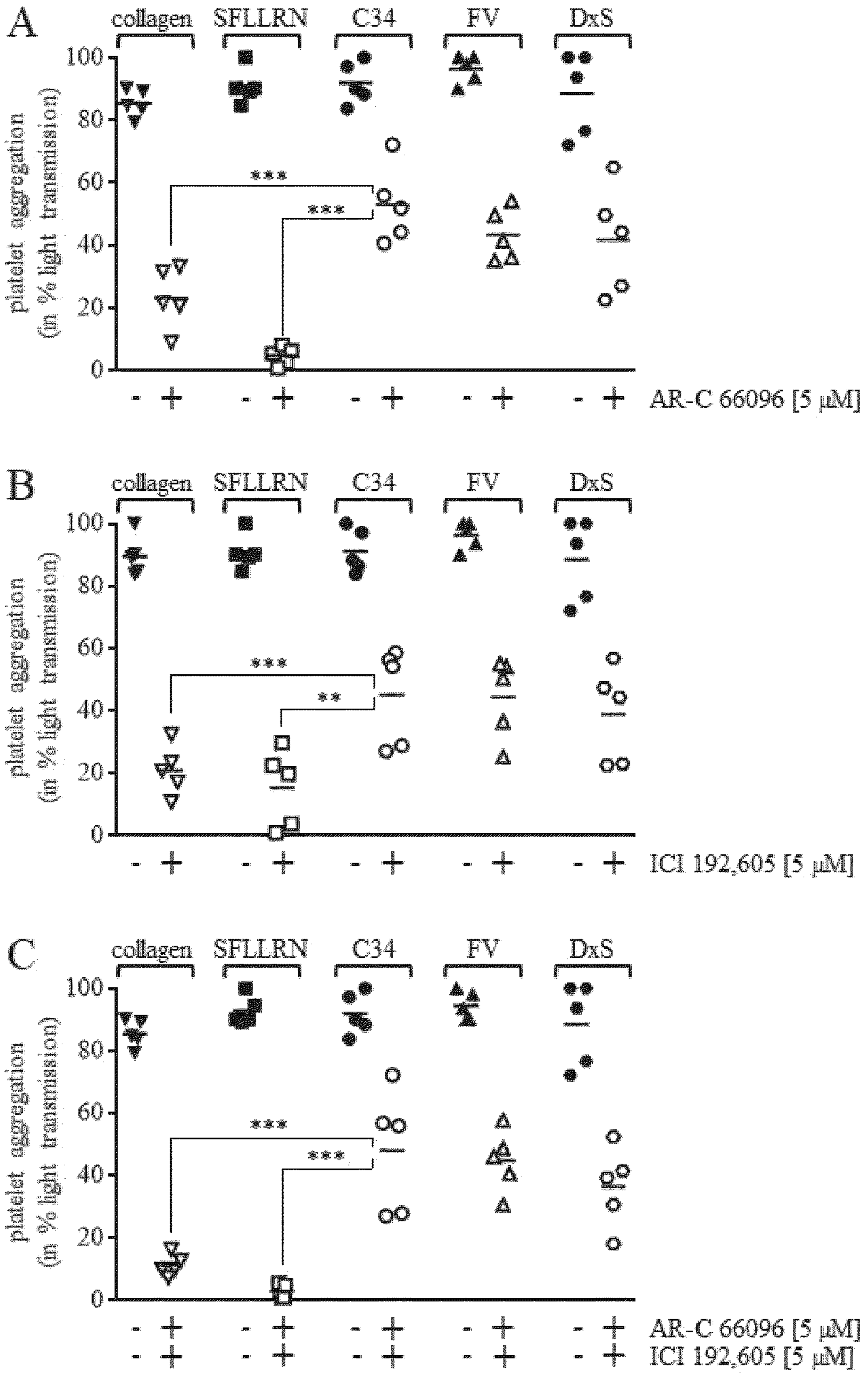
FIG. 4 shows the extent of aggregation in terms of light transmission of human platelets in plasma. (A) shows experimental results of platelet aggregation in plasma for all applied agonists (as in FIG. 3) in the presence of AR-C66096 (as a well known and accepted in vitro P2Y12 receptor antagonist). (B) shows experimental results of platelet aggregation for all applied agonists in the presence of ICI 192,506 (a potent TPα receptor antagonist). (C) shows experimental results of platelet aggregation for the above mentioned agonists in the presence of both AR-C 66096 and ICI 192,506. Platelet aggregation in terms of light transmission was recorded for 20 min. Data of n=5 experiments is presented as mean±S.E.M. and statistical analysis was performed by one-way ANOVA followed by Bonferroni's multiple comparison test; for FIG. 4A-C: $^{}P \leq 0.01$, $^{*}P \leq 0.001$, ns=not significant.

In FIG. 4 data is summarized which show that precluding either P2Y12 receptor signalling (FIG. 4A), TPα receptor signalling (FIG. 4B), or both (FIG. 4C) to various extents but markedly and significantly precluded sustained human platelet aggregation in plasma induced by collagen or the thrombin-mimetic PAR-1 agonist SFLLRN. In contrast, although mono- or dual-inhibition likewise significantly precluded the second wave of platelet aggregation in response to the synthetic sulfated α-L-fucoside-pendant glycopolymer with a chain length of 34 monomers (C34), natural fucoidan (from *F. vesiculosus*), as well as dextran sulfate, the first wave of platelet aggregation provoked by the latter three compounds remained irreversibly and sustained for the duration of assessment (20 min), and the extent of aggregation was significantly higher (except for that of dextran sulfate, which may be explained by the relatively low number of repeats, as n=5) compared to that evoked by collagen or SFLLRN.

With other words, it was found that PEAR1 receptor agonists appear to be able to induce approximately half-maximal and sustained aggregation of human platelets in plasma despite blocking P2Y12 receptor signalling, TPα receptor signalling, or both P2Y12 and TPα receptor signalling (dual inhibition; dual antiplatelet therapy; DAPT).

As such, it was found that for patients receiving mono- or dual antiplatelet medication, the use of a platelet endothelial aggregation receptor 1 (PEAR1) agonist (here fucoidans, synthetic sulfated α-L-fucoside-pendant glycopolymers, and dextran sulfate) could result in approximately half-maximal and sustained platelet aggregation. Importantly, for patients receiving antiplatelet therapies, a platelet endothelial aggregation receptor 1 (PEAR1) agonist treatment would thus be directly linked to lessening and minimizing bleeding complications.

In one embodiment, a platelet endothelial aggregation receptor 1 (PEAR1) agonist for use in the treatment of bleeding in a patient wherein the patient is under antiplatelet medication.

As such, platelet endothelial aggregation receptor 1 (PEAR1) agonists present a viable treatment option to tackle bleeding complications in a large number of patients under single or dual anti-platelet therapeutic regime.

Such treatment is normally administered at the point of bleeding for local effect, such as through topical administration of the platelet endothelial aggregation receptor 1 (PEAR1) agonists at the point of trauma or bleeding.

In one embodiment, the administration is topical administration.

In one embodiment, the administration is local administration at the point of trauma or bleeding.

For larger injuries, the extent of the injury is preferably assessed to provide information for the best treatment of the injury. In severe cases of bleeding, the administration of the platelet endothelial aggregation receptor 1 (PEAR1) agonists may be combined with other blood stopping measures, such as stiching or the temporary use of a tourniquet.

There are several different antiplatelet drugs such as acetylsalicylic acid (aspirin), nonsteroidal anti-inflammatory drugs (NSAIDs), dipyridamole, antagonists of the P2Y12 adenosine diphosphate (ADP) receptor, and inhibitors of integrin αIIbβ3 function. The combined inhibition of TXA2/TPα-signaling by e.g. aspirin and ADP/P2Y12-signalling by e.g. ticagrelor is the standard anti-thrombotic therapy.

In one embodiment, the antiplatelet medication or antiplatelet therapy comprises one or several drugs inhibiting TXA2 synthesis and/or being antagonists for the TPα receptor, and/or one or several drugs that are ADP receptor inhibitors and/or being antagonists for the P2Y12 receptor.

In one embodiment, the antiplatelet medication or antiplatelet therapy comprises one or several drugs selected from acetylsalicylic acid, triflusal, and terutroban, and/or one or several drugs selected from ticlopidine, clopidogrel, cangrelor, prasugrel, elinogrel, and ticagrelor.

Patient groups under such medications are extensive, and include stroke patients, patients with heart disease and patients who have undergone surgical procedures.

In one embodiment, the patient suffers or has suffered from a condition selected from the group consisting of stroke with or without atrial fibrillation, heart surgery, prosthetic replacement of heart valve, coronary heart disease such as stable angina, unstable angina and heart attack, patients with coronary stent, peripheral vascular disease/peripheral arterial disease and apical/ventricular/mural thrombus, coronary artery disease, heart attack, stent or coronary artery bypass graft surgery (CABG).

Antiplatelet treatment has become more and more effective, and modern antiplatelet therapies can maintain their effects for as long as 72 hours after administration. Although this is a clear advantage in terms of convenience for a patient under livelong treatment, it represents a major risk if a patient is in need of unplanned immediate surgery.

It is crucial to be able to stop bleeding during or after surgery where the patient is under antiplatelet therapy, and especially when the patient has received a high and preventative dose of the antiplatelet drug, such as within 72, 48, 24, 12, such as 6, 5, 4, 3, 2, or 1 hour. Such bleeding complications include patients receiving continuous single or dual antiplatelet medication and require immediate surgery or dental work.

In one embodiment, the bleeding is acute bleeding.

In one embodiment, the bleeding is caused by a surgical procedure.

In one embodiment, the antiplatelet medication or antiplatelet therapy has been administered to the patient within 72, 48, 24, 12, 6, 5, 4, 3, 2, or 1 hour.

One specific example of such a patient group is associated with acute aortic dissection (AD), a catastrophic manifestation in which the inner layer of the aorta tears. Blood surges through the tear from the true lumen into a false lumen, causing the inner and middle layers of the aorta to separate (to dissect), as can be seen in FIGS. 1A and 1B.

Figure 1:
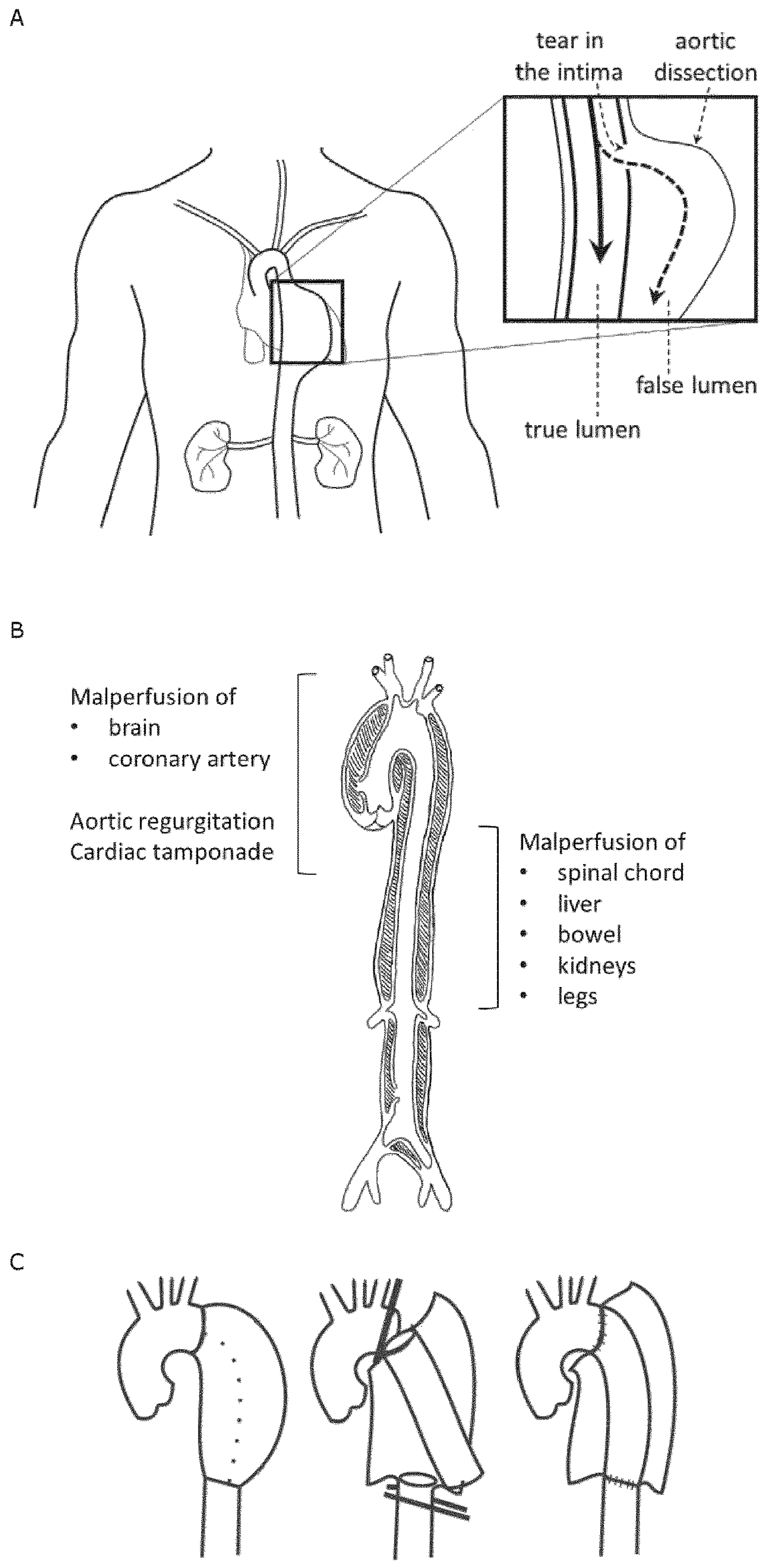

The deeper the dissection and the further the ballooning develops the more tissues are affected by malperfusion (FIG. 1B). This inadequate blood supply actually accounts for several symptomes which are similar to those of an AMI or stroke.

A Swedish population-based study of 14.229 individuals, which included a high rate of post-mortem examinations, revealed an incidence for AD of 3.4 per 100.000 people per year. Including the estimated number of unreported cases, the International Registry of Acute Aortic Dissections (IRAD) assesses incidences for AD per 100.000 people of 16 in males and 7.9 in females, respectively, with a mean age of presentation of 63 years. By comparison, in this age cohort, the incidence of experiencing an acute myocardial infarction (AMI) is approximately 400 in 100.000 inhabitants per year in Sweden (www.socialstyrelse.se).

In this respect, symptoms of AD are largely similar to those of a severe thrombotic event, such as a AMI or stroke, and may include, for instance, sudden severe chest or upper back pain, shortness of breath, sudden difficulty speaking, loss of vision, or weakness or paralysis of one side of the body. Because of these similarities and the probability of incidence, when patients are admitted to the emergency hospitalisation showing one or more of the above-mentioned symptoms, they are immediately administered a high and preventative dose of an antiplatelet drug, such as clopidogrel, cangrelor, or ticagrelor, which targets the platelet P2Y12/ADP receptors. In one embodiment, the antiplatelet medication or antiplatelet therapy comprises administering the drugs clopidogrel, cangrelor, and/or ticagrelor.

In one embodiment, the antiplatelet medication or antiplatelet therapy is a dual anti-platelet therapy (DAPT). Such therapy can be 60-90 mg ticagrelor twice daily combined with 70-100 mg aspirin.

When patients are subsequently diagnosed as experiencing an AD instead of an AMI or stroke, immediate surgery is inevitable. Normally, this entails an open thoracic aortic replacement, where the aorta is divided and a surgical Dacron interposition graft is sewn in. Surgical access is via a large cut in the left side of the chest.

At sites of the joining between the aorta and the graft, as well as at the stitching, extended bleedings occur due to the lack of platelet aggregation as the direct result of the initial admission of an ultra-high dose of a P2Y12 receptor antagonist such as clopidogrel, cangrelor, or ticagrelor.

Until bleedings stop a patient may require infusion of as many as 30 blood bags and/or spend as long as two days with an open chest in the intensive care unit. Notwithstanding the economic aspect, every blood transfusion and every minute with an opened thorax substantially increase the risk of severe infections adding to the already highly critical situation of the patient.

Thus, for patients with acute aortic dissection (AD) subjected to immediate surgery after receiving an ultra-high dose of anti-P2Y12 platelet medication, bleeding complications can be coped with and stopped using a platelet endothelial aggregation receptor 1 (PEAR1) agonist.

In one embodiment, the patient suffers from acute aortic dissection (AD).

In one embodiment, the patient has received a high dose of a P2Y12 receptor antagonist, such as ticagrelor at 180-480 mg.

In one embodiment, the patient has been initially misdiagnosed as experiencing an AMI or stroke and therefore has received a high dose of a P2Y12 receptor antagonist, such as ticagrelor at 180-480 mg.

In one embodiment, the platelet endothelial aggregation receptor 1 (PEAR1) agonist is a polysulfated polysaccharide and/or a sulfated glycopolymer. As demonstrated by the data in this application, all these agonists provoke platelet aggregation.

The sustained platelet aggregation for a sulfated glycopolymer (sulfated α-L-fucoside-pendant glycopolymer), natural fucoidan from *F. vesicolosus*, and dextran sulfate is shown in FIG. 3; and the received data summarized in FIG. 4. For all these platelet endothelial aggregation receptor 1 (PEAR1) agonists, an irreversible first wave of platelet aggregation is clearly seen despite the inhibition of TPα/TXA2 signaling, P2Y12/ADP signaling, as well as when both pathways are blocked (dual anti-platelet therapy; DAPT).

The chemical composition of natural fucoidans is extremely variable depending on eco-physiological parameters. The first structure was elucidated in 1950 from a fucoidan extracted from *F. vesiculosus*. Subsequently it has been determined that fucoidans were composed of 50%-90% of L-fucose, 35%-45% of sulfate and less than 8% of uronic acid with a linear backbone based on an α(1→2)-glycosidic linkage of O-4 sulfated L-fucose and some uses like galactose, mannose, xylose, and glucose. A revised structure of a commercial fucoidan from *F. vesiculosus* has later been published demonstrating that it mainly consists of an α(1→3)-L-fucose linear backbone with sulfate substitution at O-4 and some α-L-fucose branched at O-4 or O-2.

In one embodiment, the polysulfated polysaccharide is a fucoidan and/or a dextran sulfate.

In one embodiment, the polysulfated polysaccharide is a fucoidan.

In one embodiment, the fucodian is extracted from brown algae or brown seaweed.

In one embodiment, the fucodian is extracted from *F. vesiculosus.*

However, the heterogeneous structure of natural fucodians may pose a problem in such applications. Also, the degree of sulfation may differ between purified batches, which may directly relate to its effect. Being purified, it is hard to get a completely pure sample, and this potential batch diversity renders dosing complicated.

As such, it was recognized that synthesized fucoidan-mimetic glycopolymers, such as a sulfated α-L-fucoside-pendant glycopolymer could present several advantages.

In one embodiment, the polysulfated glycopolymer is a sulfated α-L-fucoside-pendant glycopolymer.

Fucoidan-mimetic glycopolymers can be synthezised in several different ways, such as by cyanoxyl-mediated free-radical polymerization, thiol-mediated chain transfer free-radical polymerization techniques, or RAFT polymerization. In the invention, it was found that RAFT polymerization provides unbranched polysaccharide chains and offers good control of the polymer chain length.

In one embodiment, the sulfated α-L-fucoside-pendant glycopolymer comprises an unbranched chain of pendant carbohydrates.

In the invention, artificially synthesized sulfated fucose glycopolymers (fucoidan-mimetic sulfated glucopolymers), of non-human and non-animal origin, was compared to purified fucodian. It was found that the synthezied sulfated glycopolymers evoke the same sustained effect on platelet aggregation as was observed as for the purified fucoidan (FIG. 3, FIG. 4).

The chain length was selected to provide sufficient biological activity at the applied concentration, while still being short enough to ensure synthesis of a homogeneous fraction. Further, the chain length appears appropriate to synthesize or couple the glycopolymer to a linker/adaptor protein.

Figure 5:
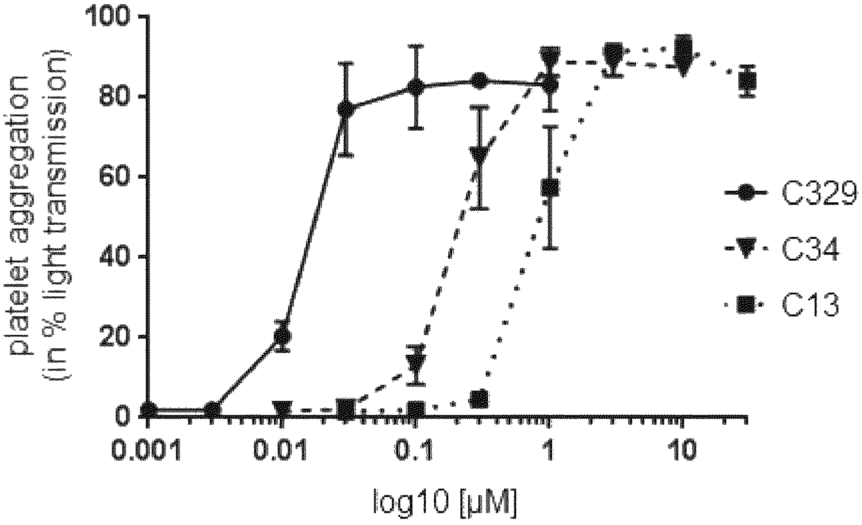
FIG. 5, shows the aggregation in terms of light transmission of isolated platelets induced by increasing concentrations of synthetic sulfated α-L-fucoside-pendant glycopolymers with monomeric chain lengths of 329 monomers (C329), 34 monomers (C34), and 13 monomers (C13).

As shown in FIG. 5, aggregation of isolated platelets is induced by fucoidan-mimetic sulfated glucopolymers of several different chain lengths. Here, chain lengths of 13, 34 and 329 monomers (monosaccharide units) all provoke full and sustained aggregation of isolated platelets (see also [3]. The shown dose-response curves clearly demonstrate that the shorter the monomeric chain length of the artificially synthesized sulfated fucose glycopolymers are, the higher concentration is required to evoke the same extent of platelet aggregation.

In one embodiment, the unbranched chain of pendant carbohydrates contains at least 10 monosaccharide units, such as at least 13 monosaccharide units.

In one embodiment, the unbranched chain of pendant carbohydrates contains from 10 to 500, such as 10 to 350 monosaccharide units, such as 13 to 329 monosaccharide units.

In one embodiment, the unbranched chain of pendant carbohydrates contains 13, 34 or 329 monosaccharide units.

The artificially synthesized sulfated glycopolymer is a sulfated α-L-fucoside-pendant poly(methacryl amide). The end product is exemplified in the formula 1 below:

Formula 1

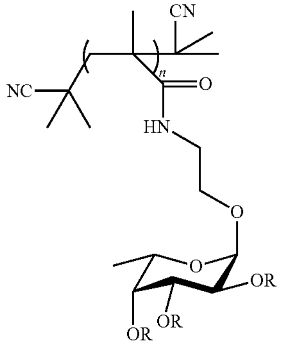

R = $SO_3Na$

In one embodiment, the sulfated glycopolymer is of the general formula 1, wherein R=$SO_3Na$. In one further embodiment, n=10 to 500, such as 13 to 329, such as 13, 34 or 329.

In one embodiment, the sulfated glycopolymer is a sulfated α-L-fucoside-pendant poly(methacryl amide).

To furnish the fucoidan-mimetic sulfated glycopolymer, all glycopolymers are O-sulfated with sulfate esters. In the invention, a high degree of sulfatation was preferred, such as over 50% of sulfatation, such as more than 60%, more than 70%, more than 80% or more than 90% degree of sulfatation.

In one embodiment, the fucoidan or sulfated glycopolymer is sulfated to a degree of at least 50%, such as at least 60%, preferrably to at least 75%, such as at least 85%. In one embodiment, the fucoidan or sulfated glycopolymer is sulfated to a degree of 50% to 100%, such as 75% to 95%, such as 85% to 90%.

The synthesized sulfated glycopolymer present several advantages. They can be highly purified, and the length can be controlled as well as the degree of sulfatation. The degree of sulfatation for the synthetized glycopolymers were all over 75%, for the synthetized glucopolymers in FIG. 5 as high as 87% degree of sulfation for C34, 89% for C13, and 87% for C329. The chain of pendant carbohydrates also simplifies linking of the synthesized fucodian-mimetic glycoploymers, and provide an even packing or layer of linked fucodian-mimetic glycoploymers.

The approximate mean molecular weight of the sulfated glycopolymer is below 500 000 g/mol, such as below 300 000 g/mol. In one embodiment, the approximate mean molecular weight of the sulfated glycopolymer is from 3500 to 275000 g/mol, such as from 7000 to 180000 g/mol.

The synthesized fucodian-mimetic sulfated glycopolymers may have integrated chemical functionalities, such as linkers for attaching the synthesized fucodian-mimetic glycopolymers to surfaces or matrices. Such features may be biotinylation for streptavidin affinity binding, PEGylation, to increase solubility, prolong stability, and reduce immunogenicity or chemical cross-linking etc.

Dextran is a complex branched glucan (polysaccharide derived from the condensation of glucose). IUPAC defines dextrans as "Branched poly-α-d-glucosides of microbial origin having glycosidic bonds predominantly C-1→C-6". Dextran chains are of varying lengths (from 3 to 2000 kilodaltons). Dextran sulfate is dextran containing approximately 13% to 21%, such as 17%, sulphur (17% is equivalent to approximately 2.3 sulfate groups per glucosyl residue). Dextran sulfate is a heparin analogue.

In one embodiment, the polysulfated polysaccharide is a dextran sulfate.

In one embodiment, the approximate mean molecular weight of the dextran sulfate is 250000 g/mol or higher, such as 250000 to 2000000 g/mol, such as 500000 g/mol or higher, such as 500000 to 2000000 g/mol.

In one embodiment, the approximate sulfur content of the dextran sulfate is from 13 to 21%, such as 15 to 19%, such as 17%.

In one embodiment, the approximate sulfur content of the dextran sulfate is approximately 1.8 to 2.8, such as 2.0 to 2.6, such as 2.3 sulfate groups per glucosyl residue.

The platelet endothelial aggregation receptor 1 (PEAR1) agonist in the invention may be in any suitable form including powders, gels, solution, or any combination of these. To facilitate use of the platelet endothelial aggregation receptor 1 (PEAR1) agonist it may also be in the form or a topical haemostatic, a sealant, or an adhesive, to be used during surgery. In the specific example of acute aortic dissection (AD), such powders, gels, solutions or topical haemostatic, sealant, or adhesive may be used at sites of the joining between the aorta and the graft, as well as at the stitching.

Topical haemostatics, sealants, and adhesives are used as normal in the art, that is until the desired effect is reached. However, in the invention, these can be used on patients under antiplatelet medication.

In one embodiment, is provided a topical haemostatic, a sealant, or an adhesive, wherein the topical haemostatic, sealant, or adhesive comprises a platelet endothelial aggregation receptor 1 (PEAR1) agonist according to any one of claims 1 to 18, for use in the treatment of bleeding in a patient, wherein the patient is under antiplatelet medication.

In one embodiment, the topical haemostatic, the sealant, or the adhesive, for use in the treatment of bleeding in a patient, wherein the use is local use.

In one embodiment, the topical haemostatic, the sealant, or the adhesive, for use in the treatment of bleeding in a patient, wherein the use is in the treatment of a bleeding in a patient during surgery.

In one embodiment, a medical patch comprising a topical haemostatic, a sealant, or an adhesive, for use in the treatment of bleeding in a patient, wherein the patient is under antiplatelet medication.

In one embodiment, a topical haemostatic, a sealant, or an adhesive, to be used locally during surgery, wherein the topical haemostatic, a sealant, or an adhesive comprises a platelet endothelial aggregation receptor 1 (PEAR1) agonist for treating bleeding in a patient under antiplatelet medication. In one embodiment, the platelet endothelial aggregation receptor 1 (PEAR1) agonist is a sulfated α-L-fucoside-pendant glycopolymer, natural fucoidan, or dextran sulfate for treating bleeding in a patient under antiplatelet medication. In one further embodiment, a medical patch comprises the topical haemostatic, sealant, or adhesive.

Materials and Methods

Chemicals

Collagen was obtained from Chrono-Log (Chrono-log Corporation, Havertown, PA, USA), the PAR1-activating peptide SFLLRN was custom-synthesized by JPT Peptide Technologies (Berlin, Germany). Fucoidan from *Fucus vesiculosus* (purity 95%) was purchased from Sigma Aldrich Sweden AB (Stockholm, Sweden). The synthetic sulfated α-L-fucoside-pendant glycopolymer with average monomeric units of 13, 34 or 329 fucose molecules was a kind gift of Prof. Peter Konradsson, Department of Physics, Chemistry and Biology (IFM)/Chemistry (KEMI), Linkoping University, Linkoping, Sweden, and was generated as described before [2, 3]. The ADP/P2Y12 receptor antagonist AR-C 66096 as well as the TXA2/TPα receptor antagonist ICI 192,605 were purchased from Tocris, UK.

Preparation of Platelet-Rich Plasma (PRP) and Platelet-Poor Plasma (PPP)

With approval from the regional ethical board Örebro-Uppsala county (Dnr 2015/543) blood was obtained from healthy volunteers, who denied to have taken any medication two weeks prior to donation, by venipuncture and drawn into 10 ml syringes preloaded by the supplier with trisodium citrate solution (Sarstedt, Nümbrecht, Germany, Order number: 02.1067.001) The blood was and centrifuged at 220 g for 20 min. The PRP thus obtained was transferred into fresh 15 ml polypropylene tubes, and the remaining blood was centrifuged at 2200 g for 20 min to separate the PPP from remaining blood cells.

Platelet Aggregation in PRP

Measurements were performed at 37° C. using Chrono-Log lumi-aggregometer (Model 700, Chrono-log Corporation, Havertown, PA, USA) with stirring at 900 rev./min using a final volume of 0.3 ml platelet suspension. Aggregation is expressed as percentage light transmission compared with PPP alone (=100%).

Platelets were preincubated with vehicle or AR-C66096 as indicated for 5 min followed by the stimulation with 1 μg/ml collagen, 10 μM SFLLRN, 30 μg/ml C34, 10 μg/ml fucoidan, or 30 μg/ml dextran sulfate (DxS) (FIG. 4A).

Platelets were preincubated with vehicle or ICI 192,506 as indicated for 5 min followed by the stimulation with 1 μg/ml collagen, 10 μM SFLLRN, 30 μg/ml C34, 10 μg/ml fucoidan, or 30 μg/ml dextran sulfate (DxS) (FIG. 4B).

Platelets were preincubated with vehicle or AR-C66096 and ICI 192,506 as indicated for 5 min followed by the stimulation with 1 μg/ml collagen, 10 μM SFLLRN, 30 μg/ml C34, 10 μg/ml fucoidan, or 30 μg/ml dextran sulfate (DxS) (FIG. 4C).

Glycopolymer Synthesis 2-methacrylamidoethyl 2,3,4-tri-O-acetyl-α-L-fucopyranoside was dissolved in 1,4-dioxane (1.20 M) and CPBDT was added. The solution was transferred to a tube containing AIBN and a stir bar and flushed with $N_2$ (g) for 30 min The tube was sealed and lowered into an oil bath pre-heated to 90° C. The solution was stirred at 90° C. for 24 h, diluted with 1,4-dioxane and freeze-dried. The crude solid compound was purified by suspension in diethyl ether, centrifuged, and isolated. This process was repeated a total of three times to yield the per-acetylated dithiobenzoate-terminated glycopolymer as a pink powder. The per-acetylated dithiobenzoate-terminated glycopolymer was then dissolved in 1,4-dioxane (0.45 mL per mmole monomer unit). The solution was transferred to a tube with a magnetic stirrer and AIBN (6.6 eq. per glycopolymer chain). The tube was flushed with $N_2$ (g) for 30 min. The tube was sealed and submerged in an oil bath pre-heated to 90° C. The solution was stirred overnight, diluted with 1,4-dioxane and lyophilized. The crude per-acetylated glycopolymer was suspended in diethyl ether, centrifuged, and isolated to yield the per-acetylated glycopolymer as a white powder. This process was performed a total of three times. The per-acetylated glycopolymer was suspended in methanol (0.08 mL per mmole monomer units), sodium methoxide (1 eq. per mole monomer units) added, and stirred overnight at RT. The solution was neutralized by Dowex Marathon C (H+), filtered and the solvent evaporated. The crude glycopolymer was dissolved in deionized water and purified by dialysis against deionized water for 48 h with frequent changes of deionized water. Lyophilization gave the glycopolymer as a white fluffy powder, glucopolymer.

To furnish the fucoidan-mimetic glycopolymers, the polymer (2) was sulfated by the following reaction: The glycopolymer was dissolved in DMF (0.01 mL per mmole monomer units) by vigorous stirring. Sulfur trioxide-pyridine complex (5 eq. per free hydroxyl group) was added and the solution stirred for 44 h at RT. The solution was decanted and the precipitated crude O-sulfated glycopolymer was dissolved in 0.9 M NaCl (aq) (90 mmole NaCl per mmole monomer units). The solution was stirred for 46 h at RT and dialyzed against 0.1 M NaCl for 19 h and then against deionized water for 24 h with frequent changes of deionized water. The resulting solution was lyophilized to give the O-sulfated glycopolymer as a white fluffy powder.

The synthesis resulted in a sulfated polymer with a degree of sulfatation of 87-89%. Calculating the effect of adding sulfates, the approximate mean molecular weight for C13 would be around 7260 g/mol, C34 would be around 16470 g/mol and C239 would be around 178300 g/mol.

Results

In the results shown in FIG. 4A, the effect of interfering with P2Y12 receptor signalling on human platelet aggregation in plasma induced by collagen, the PAR-1 activating peptide SFLLRN, the synthetic sulfated α-L-fucoside-pendant glycopolymer with average monomeric units of 34 fucose molecules (C34), natural fucoidan from *F. vesicolosus* (FV), as well as of dextran sulfate (DxS) was evaluated. AR-C66096 was used as a well-known and accepted in vitro P2Y12 receptor antagonist, a precursor finally developed into AR-C66931MX, which is better known as cangrelor, or under the trade name Plavix®. As expected is the extent of platelet aggregation induced by collagen and SFLLRN potently diminished, from 85±2% to 23±4% and 91±3% to 5±1%, respectively. The responses induced by the synthetic sulfated α-L-fucoside-pendant glycopolymer (C34: 92±3% down to 53±6%, P≤0.001), natural fucoidan from *F. vesicolosus* (FV) (96±2% down to 43±4%, P≤0.001), as well as of dextran sulfate (DxS) (84±5% down to 23±6%, P≤0.001) were also markedly and significantly affected by AR-C66096. However, the extents of these latter responses were still in all settings, with the exception of the experiments using dextran sulfate, significantly higher than those provoked be collagen or SFLLRN in the presence of AR-C66096.

As shown in FIG. 4B, we next investigated the effect of interfering with TXA2 release and subsequent TPα receptor signalling on human platelet aggregation in plasma induced by collagen, the PAR-1 activating peptide SFLLRN, the synthetic sulfated α-L-fucoside-pendant glycopolymer with average monomeric units of 34 fucose molecules (C34), natural fucoidan from *F. vesicolosus* (FV), as well as of dextran sulfate (DxS) was evaluated. Instead of using acetylsalicylic acid (ASA; aspirin) in order to prevent intercellular TXA2 synthesis, we applied ICI 192,605, a potent TPα receptor antagonist.

Platelet aggregation induced by collagen and SFLLRN were markedly reduced, from 90±3% to 21±4% and 91±3% to 15±6%, respectively. The responses induced by the synthetic sulfated α-L-fucoside-pendant glycopolymer (C34: 91±3% down to 45±7%, P≤0.001), natural fucoidan from *F. vesicolosus* (FV) (96±2% down to 44±6%, P≤0.001), as well as of dextran sulfate (DxS) (88±6% down to 39±7%, P≤0.001) were affected to a lesser extent but nonetheless significantly by ICI 192,605. Nonetheless, the extents of these latter responses were under our settings, with the exception of the experiments using dextran sulfate, significantly higher than those provoked be collagen or SFLLRN in the presence of ICI 165,605.

We finally evaluated human platelet aggregation in plasma evoked by collagen, the PAR-1 activating peptide SFLLRN, the synthetic sulfated α-L-fucoside-pendant glycopolymer with average monomeric units of 34 fucose molecules (C34), natural fucoidan from *F. vesicolosus* (FV), as well as of dextran sulfate (DxS) under conditions were both P2Y12 receptors and TPα receptors were blocked with AR-C66096 and ICI 192,605, respectively. Platelets were preincubated with vehicle or AR-C66096 and ICI 192,506 as indicated for 5 min followed by the stimulation with 1 μg/ml collagen, 10 μM SFLLRN, 30 μg/ml C34, 10 μg/ml fucoidan from *F. vesiculosus* (FV), or 30 μg/ml dextran sulfate (DxS). The results are summarized in FIG. 4C. The aggregation of platelets caused by collagen and SFLLRN were substantially inhibited, from 86±2% to 11±2% and 93±2% to 3±1%, respectively. The responses induced by the synthetic sulfated α-L-fucoside-pendant glycopolymer (C34: 92±3% down to 48±9%, P≤0.001), natural fucoidan from *F. vesicolosus* (FV) (95±2% down to 44±6%, P≤0.001), as well as of dextran sulfate (DxS) (88±6% down to 37±6%, P≤0.001) were less distinctly but still significantly reduced by the dual platelet inhibition by AR-C66096 and ICI 192,605. Nonetheless, the extents of these latter responses were under our settings, with the exception of some using dextran sulfate, still significantly higher than those provoked be collagen or SFLLRN in the presence of AR-C66096 and ICI 192,605.

Although the present invention has been described above with reference to (a) specific embodiment(s), it is not intended to be limited to the specific form set forth herein. Rather, the invention is limited only by the accompanying claims and, other embodiments than the specific above are equally possible within the scope of these appended claims, e.g. different than those described above.

In the claims, the term “comprises/comprising” does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms “a”, “an”, “first”, “second” etc do not preclude a plurality. Reference signs in the claims are provided merely as a clarifying example and shall not be construed as limiting the scope of the claims in any way.

REFERENCES

[1] C. Kardeby, K. Falker, E. J. Haining, M. Criel, M. Lindkvist, R. Barroso, P. Pahlsson, L. U. Ljungberg, M. Tengdelius, G. E. Rainger, S. Watson, J. A. Eble, M. F. Hoylaerts, J. Emsley, P. Konradsson, S. P. Watson, Y. Sun, M. Grenegard, Synthetic glycopolymers and natural fucoidans cause human platelet aggregation via PEAR1 and GPIbalpha, Blood Adv 3(3) (2019) 275-287, 10.1182/bloodadvances.2018024950.

[2] M. Tengdelius, C. J. Lee, M. Grenegard, M. Griffith, P. Pahlsson, P. Konradsson, Synthesis and biological evaluation of fucoidan-mimetic glycopolymers through cyanoxyl-mediated free-radical polymerization, Biomacromolecules 15(7) (2014) 2359-68, 10.1021/bm5002312.

[3] M. Tengdelius, C. Kardeby, K. Falker, M. Griffith, P. Pahlsson, P. Konradsson, M. Grenegard, Fucoidan-Mimetic Glycopolymers as Tools for Studying Molecular and Cellular Responses in Human Blood Platelets, Macromol Biosci 17(2) (2017), 10.1002/mabi.201600257.

[4] Alexandre Kauskot, Michela Di Michele, Serena Loyen, Kathleen Freson, Peter Verhamme, and Marc F. Hoylaerts, Anovel mechanism of sustained platelet αIIbβ3 activation via PEAR1, BLOOD, 26 Apr. 2012, Volume 119, Number 17.

The invention claimed is:

1. A method of slowing, reducing, or stopping bleeding in a patient under antiplatelet medication, comprising administering a platelet endothelial aggregation receptor 1 (PEAR1) agonist, and wherein the platelet endothelial aggregation receptor 1 (PEAR1) agonist is a fucoidan, and/or a sulfated α-L-fucoside-pendant glycopolymer.

2. The method according to claim 1, wherein the antiplatelet medication has been administered to the patient within 72, 48, 24, 12, 6, 5, 4, 3, 2, or 1 hour.

3. The method according to claim 1, wherein the antiplatelet medication comprises at least one drug inhibiting TXA2 synthesis and/or being antagonists for the TPα receptor, and/or one or several drugs that are ADP receptor inhibitors and/or being antagonists for the P2Y12 receptor.

4. The method according to claim 1, wherein the antiplatelet medication comprises at least one drug selected from acetylsalicylic acid, triflusal, and terutroban, and/or one or several drugs selected from ticlopidine, clopidogrel, cangrelor, prasugrel, elinogrel, and ticagrelor.

5. The method according to claim 1, wherein the bleeding is acute bleeding.

6. The method according to claim 1, wherein the patient suffers or has suffered from a condition selected from the group consisting of stroke with or without atrial fibrillation, heart surgery, prosthetic replacement of heart valve, coronary heart disease such as stable angina, unstable angina and heart attack, patients with coronary stent, peripheral vascular disease/peripheral arterial disease and apical/ventricular/mural thrombus, coronary artery disease, heart attack, stent or coronary artery bypass graft surgery (CABG).

7. The method according to claim 1, wherein the patient suffers from acute aortic dissection (AD).

8. The method according to claim 1, wherein the patient has been initially misdiagnosed as experiencing an acute myocardial infarction (AMI) or stroke and therefore has received a high dose of a P2Y12 receptor antagonist.

9. The method according to claim 1, wherein the sulfated α-L-fucoside-pendant glycopolymer comprises an unbranched chain of pendant carbohydrates.

10. The method e according to claim 9, wherein the unbranched chain of pendant carbohydrates contains from 10 to 500, or 10 to 350 monosaccharide units.

11. The method according to claim 1, wherein the α-L-fucoside-pendant glycopolymer is sulfated α-L-fucoside-pendant poly(methacryl amide).

12. The method according to claim 1, wherein the fucoidan and/or sulfated α-L-fucoside-pendant glycopolymer is sulfated to a degree of at least 50%, or at least 60%, or at least 75%.

13. A method of treating bleeding in a patient, the method comprising applying a topical haemostatic, a sealant, or an adhesive, wherein the topical haemostatic, sealant, or adhesive comprises a platelet endothelial aggregation receptor 1 (PEAR1) agonist according to claim 1, wherein the patient is under antiplatelet medication.

14. The method according to claim 13, wherein the applying includes applying locally at sites of acute bleeding.

15. The method according to claim 13, wherein the applying includes applying locally at sites of acute bleeding in a patient during surgery.

* * * * *